United States Patent [19]
Stoft et al.

[11] 3,987,303
[45] Oct. 19, 1976

[54] MEDICAL-ANALYTICAL GAS DETECTOR

[75] Inventors: Paul E. Stoft, Menlo Park; John A. Bridgham, Palo Alto; Robert L. Chaney, Cupertino; Charles M. Hill, Los Altos; John K. D. Lazier; Barry G. Willis, both of Palo Alto, all of Calif.; Jacob Y. Wong, Framingham, Mass.; Moshe A. Fostick, San Francisco, Calif.

[73] Assignee: Hewlett-Packard Company, Palo Alto, Calif.

[22] Filed: Feb. 6, 1975

[21] Appl. No.: 547,670

[52] U.S. Cl. .............................. 250/343; 250/351; 250/510; 356/51
[51] Int. Cl.² ..................... G21F 3/02; G21K 3/00; G01N 21/34
[58] Field of Search .......... 250/343, 351, 510, 373, 250/573; 356/51

[56] References Cited
UNITED STATES PATENTS

| | | | |
|---|---|---|---|
| 3,793,525 | 2/1974 | Burch et al. | 250/343 |
| 3,811,776 | 5/1974 | Blau | 356/51 |
| 3,878,107 | 4/1975 | Pembrook et al. | 250/343 |

*Primary Examiner*—Alfred E. Smith
*Assistant Examiner*—T. N. Grigsby
*Attorney, Agent, or Firm*—Ronald E. Grubman

[57] ABSTRACT

A gas analyzer is provided which is particularly suited for making transcutaneous measurement of the $CO_2$ concentration in the blood.

In accordance with one embodiment of the invention, sample gases from the body are circulated in a cavity of the device. A rotating wheel in the cavity includes two reference cells and a sample cell which are sequentially rotated into the optical path between a source and a detector. Three signals are thereby provided which may be combined to give an output indication of the $CO_2$ concentration in the body fluids. In a preferred embodiment, the sample cell is an "inverted cell" being in open communication with the sample gas circulating in the device so that the gas in the sample cell is a portion of the circulating gas which also surrounds the two reference cells. An output indication is thereby obtained which is insensitive to contaminants in the sample.

In accordance with another embodiment, the sample cell is isolated from the region surrounding the wheel and positioned so as to be presented in series with the reference cells in the optical detection path.

In preferred embodiments, the rotating wheel contains a number of permanent magnets which interact with a number of electromagnets driven in sequence to provide rotation of the wheel.

21 Claims, 11 Drawing Figures

MEDICAL-ANALYTICAL GAS DETECTOR

BACKGROUND OF THE INVENTION

The use of infrared gas analyzers is becoming of increasing importance in several different fields. For example, in the medical field, infrared gas analyzers may be used to monitor concentration of gases in the blood or in a sample of expired air. In conjunction with pollution control, infrared gas analyzers may be used to monitor air pollutants deleterious to the environment.

A particular method for monitoring $CO_2$ in the blood is by means of a transcutaneous measurement at the surface of the skin. Typically, the outermost layer of a small area of skin on a patient is removed, e.g., by repeated application of a strip of adhesive tape. A small pill box type device may then be sealed onto the skin so that the atmosphere in the box can come into pressure equilibrium with the body fluids in the skin. The concentration of $CO_2$ in the pill box may then be measured by a suitable infrared gas analyzer which is preferably included within the pill box.

An effective transcutaneous $CO_2$ measurement of the kind described above requires that the infrared gas analyzer be capable of providing a very rapid response time while utilizing only a small sample volume. Furthermore, the detector output should be insensitive to extraneous variables such as the intensity of any light sources employed, detector bias, and aging effects. Additionally, in medical applications of this kind the detector will be exposed to various sterilizing agents as well as contaminants present in the body fluids. The detector output should therefore be insensitive to contamination from these sources.

SUMMARY OF THE INVENTION

In accordance with one of the illustrated preferred embodiments, the present invention provides an infrared gas analyzer which is particularly suited for use in a transcutaneous $CO_2$ measurement device. The analyzer uses a single infrared source and a single detector illuminated through a single interference filter. Positioned in the optical path between the source and the detector is a rotating wheel containing two reference cells and a sample cell. The two reference cells are each enclosed between a pair of window surfaces. One of the reference cells is filled with a gas containing a standard quantity of $CO_2$, which may be mixed with an inert gas. The other reference cell contains no $CO_2$. In accordance with one embodiment of the invention, the sample gas is circulated in a region surrounding the rotating wheel. The sample cell is specially constructed to be an "open" cell directly accessible to the circulating sample gas. For example, the specially constructed sample cell may comprise a cell-like opening of the same volume as the reference cells, but having a pair of sapphire windows closely spaced to each other on only one side of the cell. Thus, a sample gas admitted to the region surrounding the rotating wheel will freely flow also into this sample cell region.

In operation, the wheel is rotated to sequentially present the two reference cells and the sample cell in the optical path between the infrared source and detector. Three signal outputs are thereby generated. The detected signal outputs during the intervals when the two reference cells are in the optical path provide two standard readings, e.g., zero and full-scale output readings. During the interval when the sample cell is in the optical path the $CO_2$ in the sample gas absorbs some radiation so that the signal amplitude is a function of the partial pressure of $CO_2$ in the sample. As will be described in more detail below, these three signals may be utilized to produce an associated output signal which is indicative of the partial pressure of $CO_2$ in the sample, and is also essentially independent of variations in the source intensity, detector efficiency, or contamination of the optical windows by contaminants in the sample.

In accordance with another of the illustrated embodiments of the invention, an analyzer is provided in which the sample cell is an enclosed cell isolated from the rotating reference cells. This embodiment of the invention is particularly suited to applications in which there is a high probability of contaminating fluids being present in the gas, e.g., in measurements of $CO_2$ in air expired from the lungs. The isolated sample cell can be easily cleaned or replaced.

In the preferred embodiments of the invention, the rotating wheel is driven by the interaction of a number of permanent magnets positioned in the wheel with electromagnetic coils mounted in the fixed housing. The electromagnetic coils are activated sequentially in response to optoelectronic signals generated from a number of optical timing marks positioned around the periphery of the wheel; very precise rotational frequency is thereby maintained. The timing marks may also be used to control external signal-processing circuitry.

DETAILED DESCRIPTION OF THE INVENTION

Figure 1:
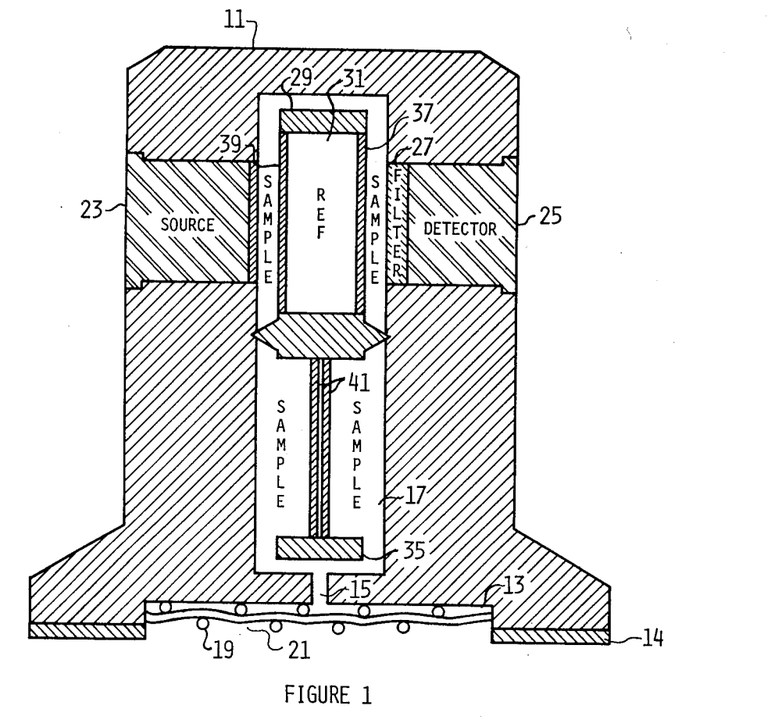
FIG. 1 illustrates a detector in which the sample gas in the sample cell is a portion of the sample gas circulating in a cavity surrounding two reference cells.

In FIG. 1 there is shown a transducer housing unit 11. Housing 11 may be fabricated from any of a number of suitable materials such as plastic or various metals; for example, devices have been built in which housing 11 is an aluminum unit of dimensions about 1 by 1 by 1. At the bottom of housing 11 is a recessed portion or chamber 13 including an opening 15 into an inner chamber 17. A screen or mesh 19 is inserted in the recessed slot 13 to stabilize the geometry of the skin-gas interface and provide gas passages from the skin into opening 15.

In accordance with procedures known to those skilled in the art, a small area of the outer layer of a patient's skin may be scraped or otherwise removed, whereupon the mesh 19 may be brought into intimate contact with the exposed area. Gases and vapors in the blood and body tissue will then diffuse into chamber 17 until an equilibrium between the composition in the chamber and that in the body is obtained. For some applications it may be desirable to utilize a thin porous membrane 21 in recess 13 to prevent body fluids from entering chamber 17, while freely admitting gases, including $CO_2$ to be measured, to equilibrate between chamber 17 and the body. To seal the chamber from the outside environment the housing must be sealed against the skin. Although various means of sealing may be used, it has been found effective to achieve sealing with a double-sided adhesive tape layer 14 affixed to housing 11.

Included within housing 11 is a source of infrared radiation 23. Any source of radiation which includes the known $CO_2$ absorption band at 4.26 $\mu$m would be a candidate for source 23. Preferably, however, a rugged small well-defined source should be employed. One such source is disclosed in copending U.S. Pat. application Ser. No. 404,845 now U.S. Pat. No. 3,875,413 entitled INFRARED RADIATION SOURCE, filed Oct. 9, 1973, by John A. Bridgham and assigned to the same assignee as the present application. An infrared radiation detector 25 is positioned opposite source 23. The detector may be any of a number of infrared detectors available in the art; e.g., a Model ATC 11 lead selenide detector available from Opto-Electronics Incorporated in Petaluma, California. Interposed between source 23 and detector 25 is an optical filter 27. This filter may be any standard filter whose characteristics include a narrow bandpass region around the carbon dioxide line at 4.26 $\mu$m.

Figure 2:
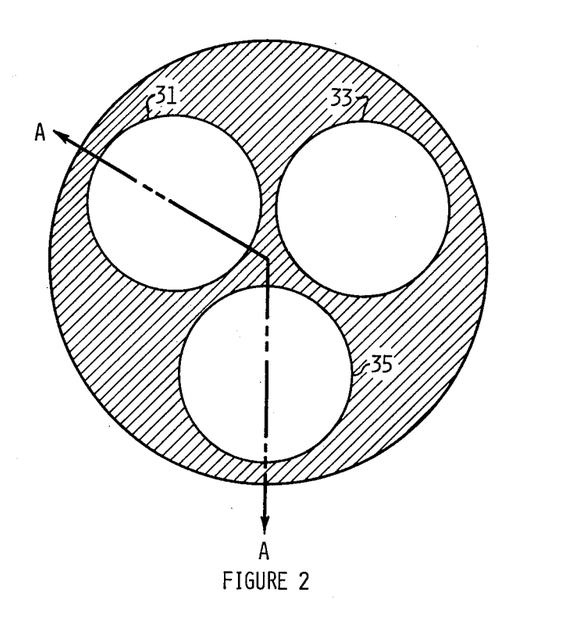
FIG. 2 shows a front view of a wheel containing two reference cells and a sample cell.

A cylindrical wheel 29 is mounted for rotation within cavity 17. A side view of wheel 29 is illustrated in FIG. 2 including a line AA along which is taken the cross-sectional view of FIG. 1. To provide best performance, the wheel should be mounted for minimum rotational friction, e.g., by using a pair of jeweled bearings (not shown).

In accordance with this embodiment of the invention, rotating wheel 29 includes three hollowed-out portions or cells. These three hollowed-out volumes labeled 31, 33 and 35 in FIGS. 1 and 2 function as two separate reference cells and a sample cell respectively. Reference cells 31 and 33 are each constructed with a pair of windows 37 and 39 which have good transmission characteristics at a desired $CO_2$ infrared absorption band. A material such as sapphire is suitable. To facilitate operation, reference cells 31 and 33 may comprise "snap in" cells which can be easily removed from or inserted into wheel 29. According to the principles of the invention, the sample cell 35 is constructed in an "inside out" configuration. By this is meant that the gas to be sampled is not enclosed in a volume between a pair of windows as are the gases in the reference cells. Instead, a pair of windows 41 are positioned back-to-back, e.g., in the center of the sample cell. Sample cell 35 is therefore an open cell in direct communication with the region 17 into which the sample gas from the body has been admitted. With the device so configured the sample gas completely surrounds all three cells so that any contaminants present in the sample will tend to contaminate windows of each of the three cells to the same extent. Consequently, as will be described in more detail below, any resulting changes in the transmission characteristics of the windows will not be reflected in the measured value of the $CO_2$ concentration. It is evident from the discussion above that windows 41 of sample cell 35 may also be displaced from the geometric center of the sample cell without altering the operation. For example, the two windows may both be placed on one side of the sample volume. Alternately, it is possible to include only one window in the sample cell. In that case, the increased optical transmission through the sample cell will simply produce an offset reading which may be compensated in the signal processing to be described shortly. For different applications, particular configurations within the spirit of the invention may be selected in accordance with ease of manufacture, cost, and the particular signal processing means employed in the device.

Figure 3:
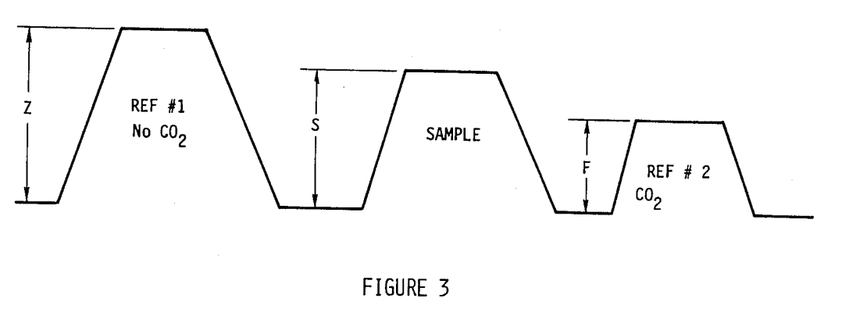
FIG. 3 is a graphical representation of the sequential signal outputs related to the two sample cells and the reference cell.

Understanding of the operation of the device may be facilitated by reference to FIG. 3 and the following discussion. One of the reference cells, e.g., cell 31, is filled with an inert gas containing a known amount of $CO_2$, e.g., no $CO_2$. When this cell is in the optical path between source 23 and detector 25 infrared absorption is a minimum and the signal amplitude output a maximum. In FIG. 3 this maximum amplitude is indicated by the letter Z (Z to indicate zero $CO_2$). The other reference cell labeled 33 is filled with a standard quantity of $CO_2$, e.g., a quantity which will yield a full-scale reading on a measuring indicator. In practice, the $CO_2$ may be mixed with an inert gas. When reference cell 33 is in the optical path, the infrared absorption is a maximum so that the signal amplitude is a minimum. In FIG. 3 this reference amplitude is designated by an F (F for full-scale absorption). Now, as was described above, the "inside out" sample cell 35 includes a volume of the sample gas in communication with the gas present in cavity 17, the optical path length through the sample cell being equal to the path length through each of the two reference cells. When sample cell 35 is in the optical path, there will be some infrared absorption, the magnitude of which is dependent on the partial pressure of $CO_2$ in the sample gas. The relative signal amplitude output during this interval will thus be reduced, for example, as indicated by the amplitude S (S for sample) in FIG. 3. In operation then, if there is no $CO_2$ present in the sample the sample signal S will be equal to the reference signal Z. If there is present in the sample an amount of $CO_2$ equal to the standard quantity of $CO_2$ present in reference cell 33, the signal S will be equal to the signal F. These relations will hold even though the sample gas in the chamber 17 is present in the optical path, since the optical path length through the "excess" sample is the same in all three cases.

In actual practice it is desirable to minimize effects of detector noise and localized window irregularities by integrating the output signals over a number of intervals when each cell is presented in the optical path. This can most conveniently be accomplished by voltage to frequency conversion methods known in the art. Other methods, e.g., analog integration may also be utilized. For purposes of explanation it is sufficient to note that the sumbols Z, S, and F may be taken to represent the integrated signals from the two reference cells and sample cell respectively. In order to determine the partial pressure of $CO_2$ in the sample an auxiliary amplitude is constructed which will be denoted by A. In accordance with the invention the amplitude A is related to the measured quantities S, Z and F by the relation $A = S-Z/F-Z$. It may be seen immediately that as the concentration of $CO_2$ varies from zero to the standard value in the reference cell 33, the amplitude A varies from zero to unity. Between these extreme values, the relationship between the partial pressure of $CO_2$ and the amplitude A is a nonlinear function which is to be determined experimentally. However, it has been determined experimentally that a unique and smoothly varying value of the partial pressure of $CO_2$ may be plotted as a function of A. Thus, the desired $CO_2$ measurement can be reliably obtained from the amplitude A. In practice, if the amplitudes are integrated by a voltage-to-frequency conversion, then several digital counters may be used to provide inputs to an on-line computer which can compute the associated amplitude and directly derive the $CO_2$ concentration.

The insensitivity of the present measurement to a large number of spurious factors may now be simply shown. For example, if a common term is added to each of the amplitudes S, Z, and F the amplitude A will be unchanged. Thus, the measurement will not be influenced by offset voltages in the detector or in any electronic signal processing used in conjunction with the detector. It is also evident that if the amplitudes S, Z, and F are all multiplied by a common factor the overall amplitude A remains unchanged. Therefore, the measurement is independent of such variables as source intensity, detector responsivity, amplifier gain, and optical attenuation in the system. In particular, any contaminants from the body or sterilizing agents which are present in the sample gas will tend to contaminate the windows of each of the three cells to about the same extent and for most contaminants this will effectively multiply each of the variables S, Z and F by a common factor as described above. The measurement will therefore be insensitive to such contamination as well.

Figure 4:
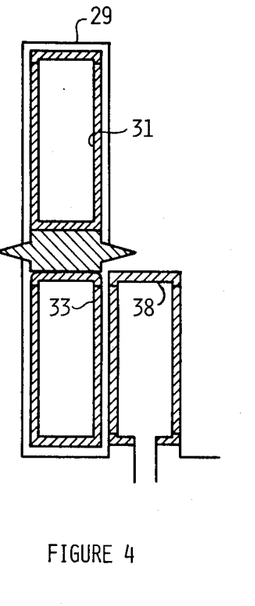
FIG. 4 illustrates a partial view of an embodiment of the invention utilizing a sample cell isolated from the region enclosing the reference cells.

In FIG. 4 there is illustrated an embodiment of the detector which is suitable for applications in which contaminants in the sample would be likely to gum-up the accurate operation of the rotating cylinder 29. This might occur if the $CO_2$ analyzer were to be employed in measuring the $CO_2$ content of air expired from the lungs of a very sick patient. For such applications, it is desirable to isolate the sample gas to be analyzed from the rotating cylinder. FIG. 4 shows a configuration including an enclosed sample cell 38 containing a sample gas to be analyzed. In this configuration, rotating wheel 29 again includes two reference cells 31 and 33 containing no $CO_2$ and a standard amount of $CO_2$ respectively. The remaining position on the wheel is now occupied by a solid mass to provide a zero reading period during which no direct radiation reaches the detector. When reference cell 33 is interposed between the sample and the detector, the $CO_2$ in the reference cell may ideally be seen as absorbing all of the radiation at the $CO_2$ absorption band; variations in the $CO_2$ concentration in the sample thus do not affect the reference reading. However, when reference cell 31 is interposed between the sample and the detector, variations in $CO_2$ concentration strongly influence the reference reading. The differences between each of these two readings and the zero (dark) reading may be used in conjunction with an initial null reading to produce a measure of $CO_2$ concentration in the sample. The initial null reading may be obtained when no $CO_2$ is present in sample cell 38. The optics associated with this embodiment may be identical to those described above in connection with FIG. 1. Thus, by using snap-in cells in wheel 29 and modifying the shape of housing 11, a detector may be provided which is readily adaptable for operation in either of the modes of FIGS. 1 or 4.

Figure 5:
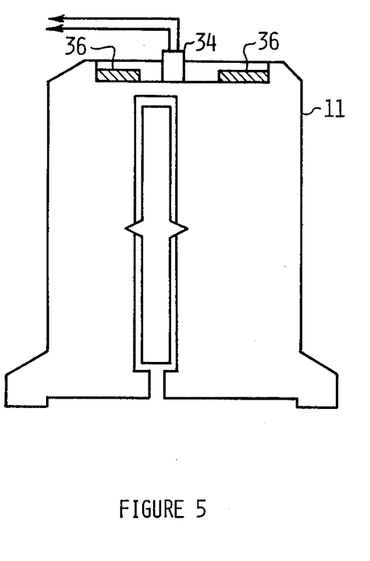
FIG. 5 illustrates a transducer including a temperature sensing and control unit.

For either mode of operation, the observed infrared absorptions vary in response to the sample $CO_2$ density in a known consistent manner. However, these absorptions also vary with temperature, and the conversion of density to partial pressure requires a knowledge of the gas temperature. It is therefore desirable to sense and control the transducer temperature. FIG. 5 illustrates a transducer including a temperature sensing and control unit.

Embedded in the transducer is a temperature sensing device 34, which may be, e.g., a thermistor. To complete the unit, a heating element 36 is positioned in thermal contact with housing 11. This element may be, e.g., a standard power transistor or an electric heating coil. By means of control circuitry (not shown) heating element 36 is responsive to temperature sensed by sensor 34. Precise control of the transducer temperature is thus provided.

It is evident from the above description that operation of the analyzer requires a drive mechanism which can accurately rotate the wheel within the hermetically sealed chamber. Generally, the conventional method of driving a rotor in a sealed chamber by means of an external motor and drive shaft through a seal is unsatisfactory for the present application; to overcome the seal friction a motor too large for the present application would be required. In accordance with the present invention, a specialized drive system is provided which utilizes minimum space and provides excellent long and short term speed stability.

Figure 6:
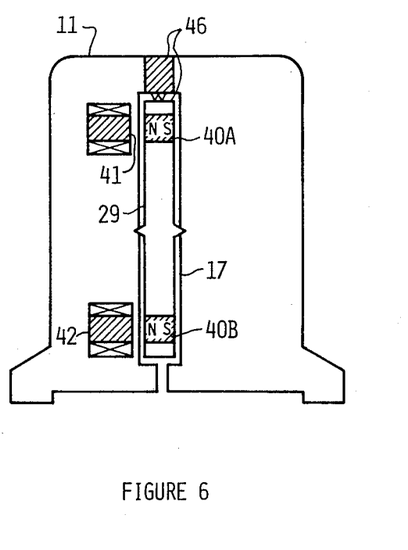
FIG. 6 is a partial view of a configuration of permanent magnets on a wheel which are driven by a number of electromagnets to produce rotation of the wheel.
Figure 7A:
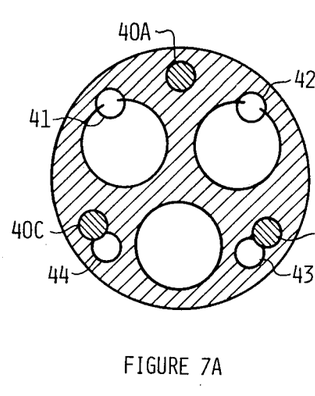
FIGS. 7A and 7B illustrate several positions of the rotating wheel relative to the electromagnets.

The mechanical construction of the drive system is shown in FIGS. 6 and 7. In FIG. 6 a schematic outline of housing 11 and rotor 29 is shown. Embedded in rotor 29 are three permanent magnets, two of which are illustrated in FIG. 6 and numbered 40A and 40B. In FIG. 7A all three permanent magnets numbered 40A, 40B, and 40C are shown. The magnets are positioned symmetrically (i.e., adjacent magnets are separated by an angular displacement of 120°). The magnetic axes of the three magnets are each positioned parallel to the rotor axis, and the poles (indicated by N and S in FIG. 6) are all aligned in the same direction. Within housing 11 but external to chamber 17 are positioned four electromagnets. Two of these numbered 41 and 42 are illustrated in FIG. 6, while FIG. 7A shows all four magnets, labeled 41, 42, 43, and 44, respectively. FIG. 6 also includes an electro-optical timing system 46, which may include e.g., a solid state light source and detector which reflects and detects light signals from a series of reflecting timing marks spaced around the periphery of rotor 29. Electrical signals generated by the timing system are used to control the drive speed, as will be discussed in detail below.

Figure 7B:
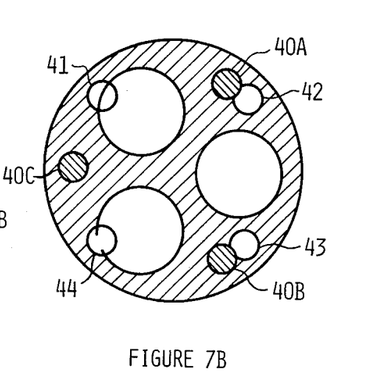

Operation of the drive may be understood by reference to FIGS. 7A and 7B. FIG. 7A illustrates an "equilibrium" position of the rotor in which the magnetic forces exerted on permanent magnets 40A–C by electromagnets 41–44 are balanced to produce a zero net torque on the rotor. In particular, electromagnet 43 is energized so as to attract magnet 40B while electromagnet 44 attracts magnet 40C; both of the electromagnets 41 and 42 are energized to repel magnet 40A, producing a net zero torque.

Figure 8:
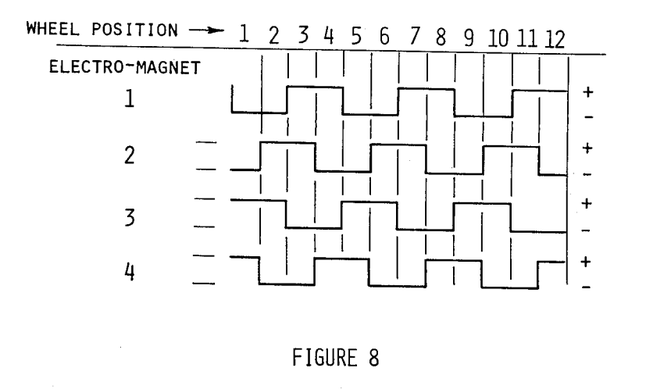
FIG. 8 shows an activation sequence for the electromagnets which provides rotation to the wheel.

Now, by reversing the polarity of the electromagnets in a particular sequence, the rotor can be rotated on-twelfth revolution clockwise to the position illustrated in FIG. 7B. By means of control circuitry to be described below, the polarity of electromagnet 44 is reversed so that it repels permanent magnet 40C while the polarity of electromagnet 42 is also reversed so as to attract permanent magnet 40A. The rotor will therefore rotate one-twelfth revolution clockwise. For continuous rotation the electromagnets are continually switched in pairs, each successive switching advancing the rotor one-twelfth revolution. FIG. 8 is a graphical representation of the switching sequence, the first stage of which was just described. A "+" indicates polarity attracting the permanent magnets, while a "−" indicates a repelling polarity. In FIG. 8, wheel position number 1 corresponds to the equilibrium position illustrated in FIG. 2A while position 2 is that illustrated in FIG. 7B.

Figure 9:
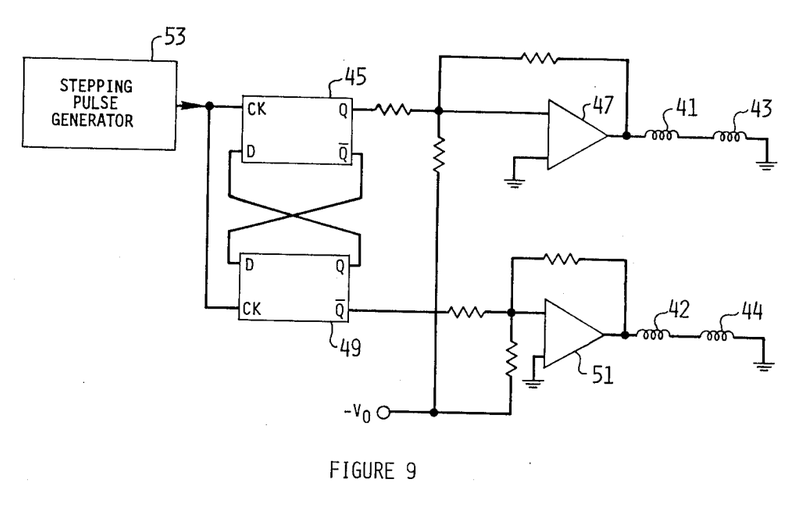
FIG. 9 is a circuit including a stepping pulse generator which drives the electromagnets.

In FIG. 9 there is illustrated schematically one simple circuit arrangement for generating the currents to be passed through coils 41–44 to achieve the switching sequence described above. Coils 41 and 43 are connected in series with a standard D-type flip-flop 45. The coils are connected with their polarities reversed to achieve the synchronized switching illustrated in FIG. 8. Similarly, coils 42 and 44 are connected in series with a D-type flip-flop 49. Two operational amplifiers 47 and 51 are interposed between the flip-flops and the coils in order to provide a plus/minus current variation rather than a zero-to-plus swing which would otherwise be present at the output of the flip-flops. A negative voltage labeled $-V_0$ provides the required offset. Flip-flops 45 and 49 are interconnected in a four state sequencer arrangement which is driven by a source of pulses from a pulse generator 53. A more detailed description of a suitable pulse generator will be given below. It will be apparent to those skilled in the art that various other arrangements of logic circuitry may also be used to generate the switching sequence of FIG. 8.

For the very accurate rotation of rotor 29 required in some applications, there are several difficulties which must be overcome. First, it can be noted that while a single source of evenly timed stepping pulses will suffice to keep the motor running at constant frequency in a continuous run mode, in order to start the motor and gradually bring it up to speed, the pulses should begin at a low rate and be gradually increased in frequency. Secondly, in applications such as the present in which there is little frictional damping of the rotor, there is likely to be present a low frequency instability of the rotor speed. Both of these problems are resolved in the present application by utilizing as a stepping pulse generator (53 in FIG. 9) a device such as that illustrated in FIG. 10. The pulse generator provides accurately timed pulses in the running mode including provision for automatic starting and restarting in the case of accidental shut-down. Additionally, the device provides for a smooth transition between starting and running modes and for critical damping of the rotor to overcome the instability mentioned above.

Figure 10:
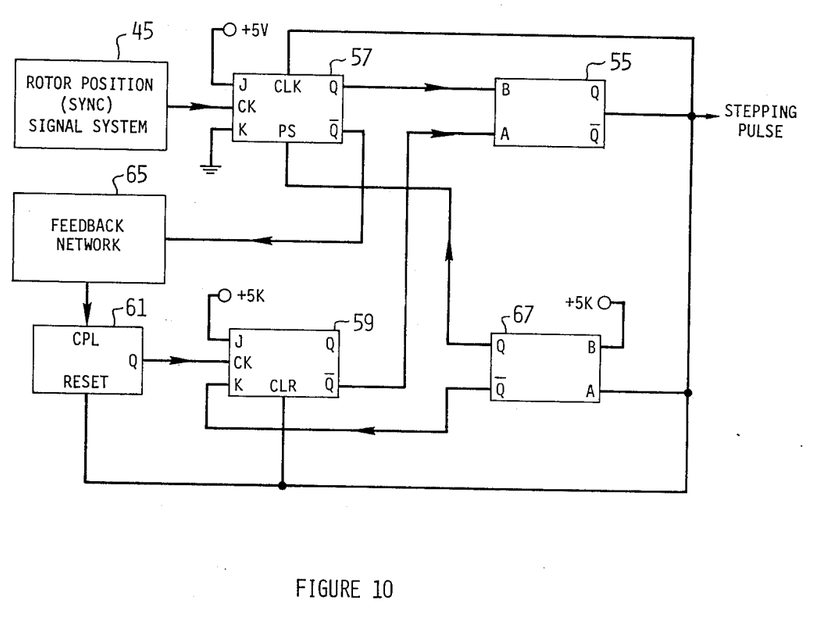
FIG. 10 illustrates an embodiment of the stepping pulse generator of FIG. 9.

Referring now to FIG. 10, the fundamental generator of the stepping pulses is a monostable multivibrator 55 which is set to generate a pulse of about 40 μs width. This pulse is simultaneously applied to the "clear" input terminals of two standard J-K flip-flops 57 and 59. Understanding of the detailed description which follows will be facilitated by noting one overall concept: the frequency of the pulses generated by multivibrator 55 is controlled at all times by one of two sources; when the rotating wheel is accelerating up to speed the pulses are responsive to a signal from the wheel via flip-flop 57. When the rotor is operating in a constant speed mode, the pulses are responsive to a signal from a preset timer via flip-flop 59. In more detail, the control scheme is as follows: multivibrator 55 will output a pulse only when activated at both terminals A and B, these two signals being the outputs of flip-flops 59 and 57 respectively. Thus, if two activating transitions arrive at terminals A and B in sequence, multivibrator 55 will effectively be triggered by the later-arriving transition, whether that activating transition be from flip-flop 57 or from flip-flop 59. Flip-flop 57 is itself triggered by a series of pulses generated by the rotating wheel through the optical system 45 described above (see FIG. 6). The frequency of these pulses from flip-flop 57 is therefore dependent on the rotor speed. Flip-flop 59 is triggered by a timer 61 which generates pulses of any desired time duration. The pulse width of the timer should preferably correspond to 1/12 the required period of a single rotor revolution. During the acceleration period of the rotor, the duration between these timer pulses will always be shorter than the interval between pulses from optical system 63. Therefore, flip-flop 59 will be clocked before flip-flop 57 and multivibrator 55 will effectively trigger on the later-received pulses from flip-flop 57, responsive to signals received from the rotating wheel. Thus, during the acceleration period the stepping pulses are increased in frequency only as the angular velocity is increased. Conversely, however, as the motor attempts to accelerate to a speed greater than that for which the timer is preset, the timer pulses will fall behind the pulses from optical system 63, so that flip-flop 57 will be triggered first and flip-flop 59 triggered later. Multivibrator 55 will therefore not put out a stepping pulse until it receives the later pulse from flip-flop 59. This retardation of the stepping pulse prevents further acceleration. The rotor will then run in a synchronous mode controlled by timer 61. To insure a smooth transition between the acceleration mode and the synchronous mode, timer 61 is reset from the stepping pulse itself so that the phase between the timer and the motor is locked prior to the transition.

The additional problem of lack of mechanical damping of the rotor possibly causing instability is compensated for by a feedback signal from flip-flop 57 via network 65 (e.g., an RC network) to provide negative feedback to the control input of timer 61. More particularly, the output of flip-flop 57 is a rectangular wave at the stepping pulse frequency with a duty cycle proportional to the phase between the timer pulses and those received from the rotating wheel. Filter network 65 passes those frequency components of this signal that are associated with the frequency of phase instability (typically a few Hz) while blocking d.c. and the stepping pulse frequencies. If a phase transient is introduced (as might occur if the transducer were suddenly rotated in the course of normal handling) the pulse rate of timer 61 will be altered momentarily by the feedback signal to reduce the phase error. By suitably choosing the pass band attenuation of network 65 critical damping of the rotor drive system may be achieved.

Finally it is important that pulses be available to initially start the motor and at any other time that the motor might accidentally stop due to mechanical shock, momentary power failure, etc. This capacity is provided by a monostable multivibrator 67 set to generate pulses at a predetermined interval, for example, 0.5 second. If for any reason the stepping pulses fail for longer than about 0.5 second, the multivibrator 67 will output a pulse to set flip-flop 57 and switch flip-flop 59 into a toggle mode. Thus, so long as power is supplied to multivibrator 67, it is assured that multivibrator 55 will be triggered and pulses generated to start or restart the system.

We claim:

1. A device for detecting a component gas in a sample gas comprising:
    a housing;
    source means mounted within the housing for providing radiation in a preselected spectral band having at least one absorption line of the component gas to be detected;
    detector means mounted in the housing for detecting radiation in the preselected spectral band;
    a plurality of reference cells, each reference cell containing a reference gas including a standard amount of said component gas to be detected;
    a sample cell for containing a quantity of sample gas including the component gas to be detected; and
    sequencer means in the housing for introducing in time sequence each of the reference cells and also the sample cell into an optical path between the source means and the detector means;
    said detector means being responsive to radiation incident thereon when each of the reference cells is in the optical path and when the sample cell is in the optical path, for producing thereby a plurality of detector output signals whose amplitudes are dependent on the amount of the component gas which may be present in the plurality of reference cells and the sample cell respectively said plurality of signals being operable in predetermined formulation to provide an indication of the concentration of the component gas in the sample gas.

2. A device as in claim 1 wherein:
    the plurality of reference cells comprises a first reference cell for containing a first reference gas including a first standard amount of said component gas to be detected, and a second reference cell for containing a second reference gas including a second standard amount of the component gas to be detected; and
    said detector means is responsive to radiation incident thereon when each of the three cells is in the optical path, for producing thereby three detector output signals whose amplitudes are dependent on the amount of the component gas which may be present in the first reference cell, the second reference cell, and the sample cell respectively, said three signals being operable in predetermined formulation to provide an indication of the concentration of the component gas in the sample gas.

3. A device as in claim 2 wherein:
    the housing has a cavity for circulating therein a volume of the sample gas; and
    the sample cell comprises a cell in open communication with the cavity for containing a quantity of sample gas which is a portion of the volume of sample gas circulating within the cavity.

4. A device as in claim 3 wherein the sequencer means comprises a rotating wheel in which the first and second reference cells and the sample cell are positioned.

5. A device as in claim 4 further comprising:
    a plurality of permanent magnets embedded in the rotating wheel; and
    a plurality of electromagnets included within the housing for activation in a predetermined sequence to attract and repel the permanent magnets embedded in the wheel, thereby inducing rotation of the wheel.

6. A device as in claim 5 further comprising:
    a plurality of timing marks spaced around the periphery of the rotating wheel; and
    electro-optical means for reflecting optical signals from the timing marks to generate electrical signals for controlling the speed of the rotating wheel.

7. A device as in claim 6 further comprising:
    temperature sensing means for detecting the temperature of the gas in the sample cell; and
    temperature control means responsive to the temperature sensing means for maintaining the temperature of the gas in the sample cell at a desired temperature.

8. A device for use in measuring the concentration of a component gas in the fluids of a human body, said device comprising:
    a housing;
    source means mounted with the housing for providing radiation in a preselected spectral band having at least one absorption line of the component gas to be detected;
    detector means mounted in the housing for detecting radiation in the preselected spectral band;
    a plurality of reference cells, each reference cell containing a reference gas including a standard amount of said component gas to be detected;
    a sample cell for containing a quantity of sample gas including the component gas to be detected;
    sequencer means in the housing for sequentially introducing the reference cells and the sample cell into an optical path between the source means and the detector means; and
    a screening member mounted in a recessed chamber in communication with the sample cell for maintaining a stable geometry of an interface between the recessed chamber and a region of the skin surface of the body when the device is brought into intimate contact with said region;
    said detector means being responsive to radiation incident thereon when each of the reference cells and the sample cell is in the optical path, for producing thereby a plurality of detector output signals whose amplitudes are dependent on the amount of the component gas which may be present in the plurality of reference cells and the sample cell respectively, said plurality of signals being operable in predetermined formulation to provide an indication of the concentration of the component gas in the sample gas.

9. A device as in claim 8 further comprising:
    a membrane stretched across the recessed chamber for allowing gases from the human body to enter the cavity in the housing while preventing the passage of body fluids thereinto.

10. A device as in claim 8 further comprising:
    an adhesive on a portion of the housing in contact with the skin to provide a sealed region between the sample cell and the body.

11. A device as in claim 8 for use in measuring the concentration of said component gas in the fluids of a human body, wherein:

the sequencer means comprises a wheel operable for introducing in time sequence each of the reference cells and also the sample cell into the optical path between the source means and the detector means; and the detector means is responsive to radiation incident thereon when each of the reference cells is in the optical path and when the sample cell is in the optical path for producing thereby a plurality of detector output signals whose amplitudes are dependent on the amount of the component gas which may be present in the plurality of reference cells and the sample cell respectively, said plurality of signals being operable in predetermined formulation to provide an indication of the concentration of the component gas in the sample gas.

12. A device as in claim 11 wherein:

the housing has a cavity for circulating therein a volume of the sample gas; and the sample cell comprises a cell in open communication with the cavity for containing a quantity of sample gas which is a portion of the volume of sample gas circulating within the cavity.

13. A device as in claim 12 further comprising:

a plurality of permanent magnets embedded in the rotating wheel; and a plurality of electromagnets included within the housing for activation in a predetermined sequence to attract and repel the permanent magnets embedded in the wheel, thereby inducing rotation of the wheel.

14. A device as in claim 13 further comprising:

a plurality of timing marks spaced around the periphery of the rotating wheel; and electro-optical means for reflecting optical signals from the timing marks to generate electrical signals for controlling the speed of the rotating wheel.

15. A device as in claim 14 further comprising:

temperature sensing means for detecting the temperature of the gas in the sample cell; and temperature control means responsive to the temperature sensing means for maintaining the temperature of the gas in the sample cell at a desired temperature.

16. A device as in claim 8 for use in measuring the concentration of said component gas in the fluids of the human body, wherein:

the sequencer means comprises a rotating wheel operable for introducing in time sequence said plurality of reference cells into said optical path;

the sample cell is positioned adjacent said wheel for operation in series with each reference cell in the optical path between the source and the detector; and the detector means is responsive to radiation incident thereon when each of the reference cells is in series with the sample cell in the optical path for producing thereby a plurality of detector output signals whose amplitudes are dependent on the amount of the component gas which may be present in the plurality of reference cells and the sample cell respectively, said plurality of signals being operable in predetermined formulation to provide an indication of the concentration of the component gas in the sample gas.

17. A device as in claim 16 further comprising:

a membrane stretched across the recessed chamber for allowing gases from the human body to enter the cavity in the housing while presenting the passage of body fluids thereinto.

18. A device as in claim 17 further comprising:

an adhesive on a portion of the housing in contact with the skin to provide a sealed region between the sample cell and the body.

19. A device as in claim 16 further comprising:

a plurality of permanent magnets embedded in the rotating wheel; and a plurality of electromagnets included within the housing for activation in a predetermined sequence to attract and repel the permanent magnets embedded in the wheel, thereby inducing rotation of the wheel.

20. A device as in claim 17 further comprising:

a plurality of timing marks spaced around the periphery of the rotating wheel; and electro-optical means for reflecting optical signals from the timing marks to generate electrical signals for controlling the speed of the rotating wheel.

21. A device as in claim 18 further comprising:

temperature sensing means for detecting the temperature of the gas in the sample cell; and temperature control means responsive to the temperature sensing means for maintaining the temperature of the gas in the sample cell at a desired temperature.

* * * * *

UNITED STATES PATENT AND TRADEMARK OFFICE
CERTIFICATE OF CORRECTION

PATENT NO. : 3,987,303
DATED : October 19, 1976
INVENTOR(S) : Paul E. Stoft, et al.

It is certified that error appears in the above-identified patent and that said Letters Patent are hereby corrected as shown below:

Column 2, line 63, "1 by 1 by 1.", should read -- 1" by 1" by 1". --;

Signed and Sealed this

First Day of February 1977

[SEAL]

Attest:

RUTH C. MASON
Attesting Officer

C. MARSHALL DANN
Commissioner of Patents and Trademarks